United States Patent [19]

Froome

[11] 4,364,271
[45] Dec. 21, 1982

[54] OPTICAL REFRACTOMETER

[75] Inventor: Keith D. Froome, Hampton, England

[73] Assignee: National Research Development Corporation, London, England

[21] Appl. No.: 149,558

[22] Filed: May 13, 1980

[30] Foreign Application Priority Data

May 31, 1979 [GB] United Kingdom ................ 7918959

[51] Int. Cl.³ .......................... G01W 1/02; G01N 9/00
[52] U.S. Cl. .................................... 73/432 R; 73/30; 73/384; 356/128; 374/142
[58] Field of Search ............... 356/128; 73/384, 386, 73/345, 432 R, 701, 708, 718, 30, 170 R

[56] References Cited

U.S. PATENT DOCUMENTS 4,000,652 1/1977 Wiklund ........................... 73/30 X

FOREIGN PATENT DOCUMENTS 1334496 10/1973 United Kingdom .
1425745 2/1976 United Kingdom .
1472543 5/1977 United Kingdom .

Primary Examiner—James J. Gill
Attorney, Agent, or Firm—Cushman, Darby & Cushman

[57] ABSTRACT

A terrestrial refractometer comprising a gastight enclosure of substantially invariant transverse section and having a linearly movable endwall which varies in position in accordance with ambient temperature and pressure, the enclosure containing a fixed mass of a gas which at least approximates to an ideal gas; sensing means responsive to the linear position of the endwall; and compensating means arranged to apply a compensating factor which is proportional to the linear movement by the endwall from its position under conditions of standard temperature and pressure.

10 Claims, 7 Drawing Figures

OPTICAL REFRACTOMETER

This invention relates to refractometers, that is, devices which can provide a signal relating to refractive index.

It may be a requirement of physical measurements over long distances on the earth's surface, such as, for example, electromagnetic distance measurements at optical wavelengths, that an accurate measure is available of the refractive index of the terrestrial atmosphere through which the measurement is made. In one method this is obtained by separate measurements of temperature and pressure; corrections for refractivity are then made by reference to tables or use of a special slide rule. In another method, as described in the specification of UK Pat. No. 1425745, an automatic correction is applied by using the properties of a fixed mass of ideal gas constrained in a flexible bellows, the expansion and contraction of the bellows varying with ambient temperature and pressure, and the movement being used to provide a correction factor. However, the described method and apparatus may not provide a completely accurate correction factor, because the inherent springiness or stiffness of the bellows resists both expansion and contraction.

The present invention relates to an improved device which can provide a signal related to the refractive index under ambient conditions of temperature and pressure of the air near the surface of the earth, and the device will heretofore be referred to as a terrestrial refractometer.

According to the invention, a terrestrial refractometer comprises a gastight enclosure of substantially invariant transverse section and having a movable endwall which varies linearly in position in accordance with ambient temperature and pressure, the enclosure containing a fixed mass of a gas which at least approximates to an ideal gas; sensing means responsive to the linear position of the endwall; and compensating means arranged to apply a compensating factor which is proportional to the linear distance moved by the endwall from its position under conditions of standard temperature and pressure.

The gastight enclosure is conveniently the metal bellows of an aneroid barometer, when the resistance to the expansion or contraction of the bellows, causing linear movement of the endwall of the bellows, is the stiffness of the bellows or the springiness of the metal. It is assumed, according to the invention, that the resistance of the bellows to expansion or contraction is proportional to the magnitude of the movement from a zero position, conveniently the position at standard temperature and pressure.

In a first arrangement, the compensating means comprises a part of the sensing means which responds to linear movement of the movable endwall in the required manner. For example, there may be a simple readout-scale with a non-linear calibration, or an electrical position-sensor providing the appropriate response.

In a second arrangement, the compensating means comprises movement-assistance means arranged to apply to the movable endwall a force in the direction of movement which is proportional to the magnitude of the movement. The result is that the bellows expansion or contraction is assisted to overcome resistance to the movement so that the full theoretical movement is achieved. Conveniently, the sensing means then comprises an electrical capacitor arranged to sense the position of the endwall.

The invention will now be described by way of example with reference to the accompanying drawings in which.

First, consider the refractive index of the earth's atmosphere at sea level; the value changes by about 1 part per million when there is a pressure change of 2.7 millimeters of mercury (3 millibars) or a temperature change of 1° C. Let the refractive index under standard temperature and pressure To, Po (0° C. or 15° C. and 760 millimeters of mercury, 1013 millibars), be $n_o$ and under ambient conditions $P_x$ $T_x$ be $n_x$. Then:

$$(n_x - 1) = (n_o - 1) \frac{P_x}{P_o} \cdot \frac{T_o}{T_x} \quad [1]$$

Thus $dn = (n_o - 1) - (n_x - 1) = (n_o - 1) \left[ 1 - \frac{P_x}{P_o} \frac{T_o}{T_x} \right]$ It is to be understood that the equations given above hold at sea level and at heights up to ten (or more) thousand feet; that is, the refractometer according to the invention is essentially a terrestrial instrument.

Further, it is well known that the value of $n_o$ is a function of the optical wavelength at which it is measured, but is insensitive to atmospheric water vapour pressure, which therefore need not be considered.

Consider a rigid cylinder in which a fixed mass of an ideal gas is constrained by a freely movable piston. From the gas laws:

$P_o V_o = RT_o$ at standard temperature and pressure, and $P_x V_x = RT_x$ at ambient conditions.
Therefore $$V_x - V_o = \frac{RT_o}{P_o} \left[ \frac{P_o}{P_x} \frac{T_x}{T_o} - 1 \right] \quad [2]$$

Comparisons of equations [1] and [2] show that the movement of a piston under changes of temperature and pressure is the inverse of the variation with temperature and pressure of the refractive index of the atmosphere, provided the piston achieves the full theoretical movement.

In practice, the piston and cylinder is conveniently an aneroid barometer bellows filled with dry air. The bellows has considerable stiffness or springiness which must be compensated.

Figure 1:
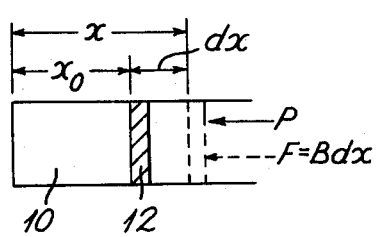
FIG. 1 illustrates the principle of a first compensating means according to the invention.

One principle of bellows stiffness-compensation is illustrated schematically in FIG. 1. Suppose that at ambient conditions $P_x$ $V_x$ $T_x$ the freely movable piston 12 has moved from position $x_o$ to position x, where $dx = x - x_o$. Assume that the stiffness of the bellows is proportional to the displacement. The force F on the bellows is then $F = B \, dx \quad [3]$ where B is a constant. Also:

$$V_x = K_1 x$$

where $K_1$ is a constant: thus:

$$V_x - V_o = Adx$$

Also $P_x = P + F = P + Bdx$

At standard conditions:

$$Ax_o = (RT_o/P_o)$$

and at ambient conditions:

$$Ax = (RT_x/P + Bdx)$$

Thus $dx = x - x_o = \dfrac{R}{A}\left[\dfrac{T_x}{P + Bdx} - \dfrac{T_o}{P_o}\right]$ [4]

But $dn = (n_o - 1)\left[1 - \dfrac{P_x}{P_o} \cdot \dfrac{T_o}{T_x}\right]$ [2]

Therefore:-

$$dn = (n_o - 1)\left[1 - \dfrac{T_o}{T_x}\dfrac{(P + Bdx)}{P_o} + \dfrac{Bdx}{P_o} \cdot \dfrac{T_o}{T_x}\right]$$ [5]

From equation [4], $$P + Bdx = \dfrac{RT_x P_o}{P_o Adx + RT_o}$$

Substituting in equation [5]:

$$dn = (n_o - 1)\left[1 - \dfrac{1}{1 + \dfrac{P_o Adx}{RT_o}} \cdot \dfrac{Bdx}{P_o} \cdot \dfrac{T_o}{T_x}\right]$$

But $\dfrac{P_o}{T_o} = \dfrac{R}{V_o} = \dfrac{R}{Ax_o}$, so $\dfrac{P_o Adx}{RT_o} = \dfrac{dx}{x_o}$ Putting $B = fP_o$, where f is the springiness of the bellows, then $$dn = (n_o - 1)\left[1 - \left(1 + \dfrac{dx}{x_o}\right)^{-1} + fdx\dfrac{T_o}{T_x}\right]$$ [6]

If $dx/x_o$ is small, say 1/5 or less, then terms higher than $dx^3$ can be neglected in a binomial theorem expansion. Thus:

$$dn \, \Omega \, (n_o - 1) \, dx \left[\dfrac{1}{x_o} + \dfrac{fT_o}{T} = \dfrac{dx}{x^2}\right]$$

Or, putting $T_x = T_o + t$, where t is temperature in °C:

$$dn \, \Omega \, (n_o - 1) \, dx \left[\dfrac{1}{x_o} + \dfrac{f}{1 + \dfrac{t}{T_o}} - \dfrac{dx}{x^2}\right]$$ [7]

Typically with an aneroid barometer bellows $x_o = 1$ centimeter and $f = 0.1$.

It will be seen that the effect of temperature is small, and adequate compensation can be provided by a thermistor or a mercury-in-glass thermometer.

Figure 2:
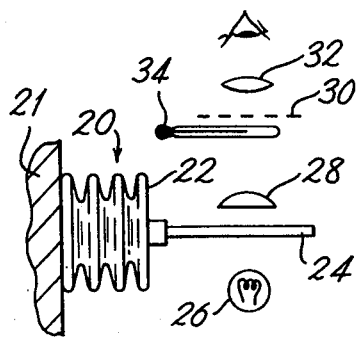
FIGS. 2, 3 and 4 illustrate three terrestrial refractometers based on the first compensating principle.
Figure 3:
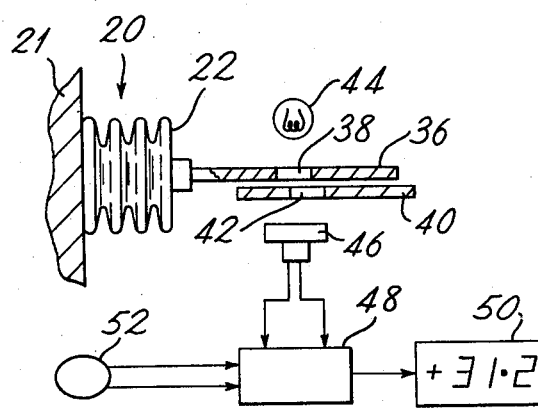
Figure 4:
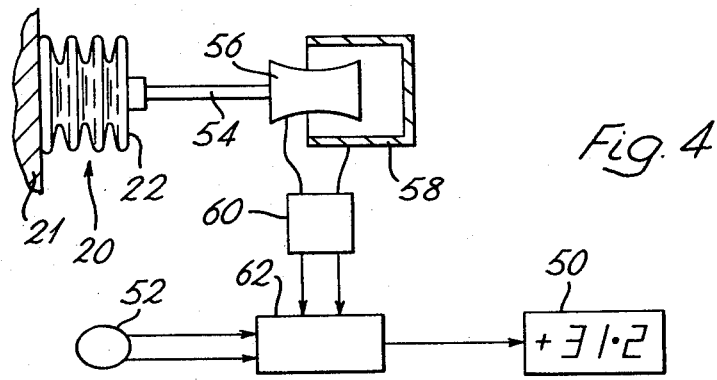

The equation is non-linear and the embodiments shown in FIGS. 2 to 4 include features which apply compensation in a non-linear manner.

In FIG. 2, a bellows 20 is fixed at one end to an insulating support 21; the other, freely movable end 22 carries a transparent scale 24 calibrated in accordance with equation [7]. The scale is illuminated by a light source 26; an objective lens 28 provides a magnified image of the scale at position 30 and this image is viewed through an eyepiece lens 32. Adjacent the image at 30 and fixed in position is a mercury-in-glass thermometer 34; if the scale is viewed so that the mercury meniscus is used as a reference, and the scale reading indicated by the meniscus is noted, then adequate temperature compensation has been provided. To allow for variation of refractive index with wavelength, several calibrations may be provided and the scale 34 can be movable perpendicular to the plane of the drawing to allow selection.

In FIG. 3, the movable end of the bellows 22 carries a plate 36 having in it a slit 38; a fixed plate 40 with a slit 42 is placed close to the movable slit. The slits are illuminated by a light emitting diode 44, and light passing through them falls on a photodiode 46 connected to an electronic calculating and wavelength selection circuit 48 which has a digital display 50. A thermistor 52 provides temperature compensation.

As the bellows expands or contracts, the amount of light passing through the movable and fixed slits varies; the slits are shaped so that the variation is in accordance with equation [7]; the display gives a digital readout of dn.

In FIG. 4 the movable end of the bellows 22 carries an insulating rod 54 which supports the first metal cylinder plate 56 of a variable capacitor; the second plate 58 is a fixed metal cylinder. The first plate is shaped so that as it moves with respect to the fixed plate, the capacity varies in accordance with equation [7]. The capacity is sensed by a suitable circuit 60, such as a capacity controlled oscillator or a capacity sensing bridge circuit; the value of the measured capacity is supplied to a calculating circuit 62 having a readout 50 and which is temperature-compensated by a thermistor 52.

As an alternative to a variable capacitor, a variable inductor could be used.

In the embodiments illustrated in FIGS. 2, 3 and 4, compensation in accordance with equation [3] is applied by means of read-out systems having non-linear features. An alternative principle of compensation is to apply an actual force to the bellows in accordance with equation [3]. This principle is used in the embodiments illustrated in FIGS. 5, 6 and 7.

Figure 5:
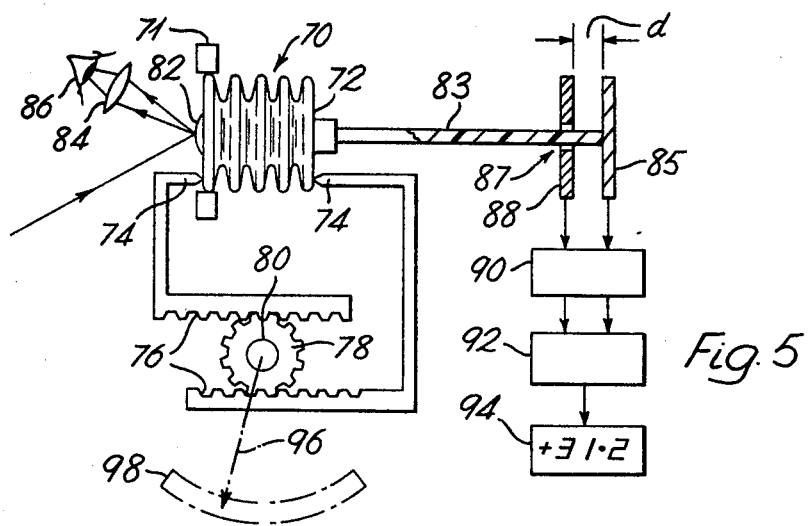
FIGS. 5, 6 and 7 illustrate three terrestrial refractometers based on a second compensating principle.

In FIG. 5, an aneroid barometer bellows 70 contains a fixed mass of dry air, which approximates to an ideal gas. The bellows is supported near one end by an insulating support 71, and the other end 72 is free to move, allowing expansion or contraction as ambient temperature and pressure change. The bellows are made of metal, and the springiness of this material, or the stiffness, often prevents the full degree of expansion or contraction, thus causing errors in the refractometer.

To overcome this, compensation means is provided in the form of a rack and pinion arrangement. The bellows is held between a pair of jaws 74, fixed to the bellows endwalls to provide both expansion and contraction forces, and the jaws are rigidly attached to parallel racks 76 on opposite sides of a pinion wheel 78 which has a manual adjusting knob 80.

The fixed end of the bellows is in the form of a thin polished membrane 82 illuminated by a collimated light beam (not shown) and which can be viewed through a lens 84 by an eye at position 86. If the pressures inside and outside the bellows are unequal, the membrane is curved; if the pressures are equal, the membrane is flat and the eye sees a disc of maximum brightness. The knob 80 is adjusted, moving the jaws 74 closer or futher apart as required and therefore contracting or expanding the bellows by applying force F=Bdx until the maximum brightness condition is reached and pressure inside the bellows equals ambient pressure.

To provide a measure of the position of the movable bellows endwall 72, and thus of volume V, the endwall is attached to an insulating rod 83 which carries a metal plate 85 forming one half of a parallel plate condenser 87. The other plate 88 is nearer the bellows, the rod 83 passing through a central aperture. The plates are connected to a capacity sensing circuit 90, such as a capacity controlled oscillator or a capacity-sensing bridge circuit, which in turn is connected to an electronic calculating unit 92 having a visual display 94.

Suppose the plates 85, 88 are of area A and spacing d. The value d is proportional to the volume V of the bellows. At standard temperature and pressure:

$$C_o = \frac{A}{4\pi d_o} = \frac{K}{V_o}$$

and at ambient conditions:

$$C = \frac{A}{4\pi d} = \frac{K}{V}$$

where $C_o$, $C$ are values of the condenser capacity and K is a constant.

$$\text{Thus } C_o - C = \frac{K}{V_o} - \frac{K}{V} \quad [8]$$

$$= \frac{K}{R}\left[\frac{P_o}{T_o} - \frac{P}{T_x}\right]$$

$$= \frac{KP_o}{RT_o}\left[1 - \frac{P}{P_o}\frac{T_o}{T_x}\right]$$

Equation [8] is of the same form as equation [2], so that the value of dn can be derived by the calculating unit 92 from a measure of the change in capacity C.

Alternatively, a mechanical readout can be provided by an optical pointer 96 and scale 98, the scale being calibrated as the inverse of the bellows movement.

Refractive index varies with wavelength, and in either arrangement several scales may be provided and the appropriate one selected.

Figure 6:
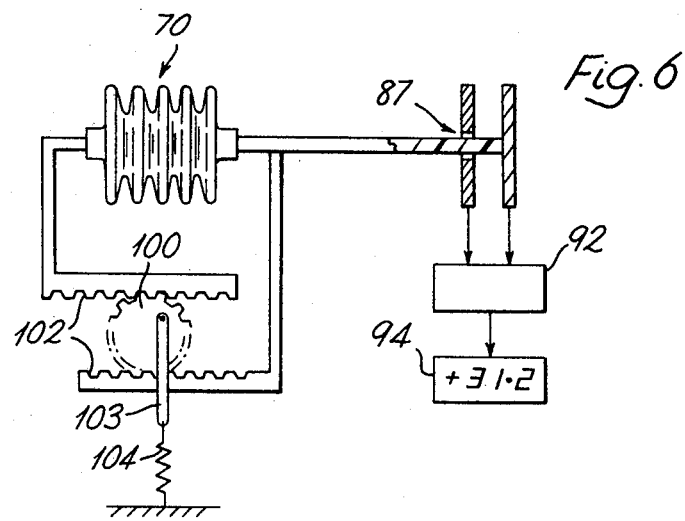

In FIG. 6, automatic compensation for the bellows stiffness is provided by a pinion wheel 100 and two parallel racks 102 rigidly connected one to each end of the bellows 70 and also supporting the bellows. The pinion wheel 100 is pivotally connected near its highest point to a connecting link 103 connected at its further end to a tensioned helical spring 104. The capacitor 87 and calculating unit 92 are identical to those in FIG. 5.

At standard temperature and pressure the pinion is arranged with the pivot at the highest point so that no force is applied to the bellows 70. As the bellows expand or contract, the racks are moved in opposite directions, the pinion wheel 100 rotates so the pivot is no longer at its highest point, and the spring applies a force to the bellows through the link 103, pinion 100 and racks 102 in such a direction that the movement of the bellows is assisted and of such magnitude that bellows stiffness is compensated in accordance with the equation F=Bdx [3]. This is achieved by setting the helical spring to the appropriate tension with the bellows unsealed; resistance to movement is then entirely due to stiffness or springiness.

Figure 7:
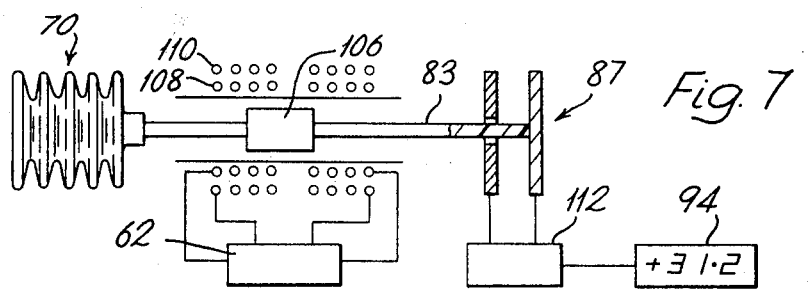

In FIG. 7 a third compensation arrangement is shown. The insulating rod 83 carries a ferrite core 106 which lies partly within a double-wound solenoid. One winding 108 acts as a position sensor and one winding 110 acts as an energiser; both windings are connected to an electronic unit 112. As the bellows expand or contract, the ferrite core 106 is moved within the sensing winding which passes a signal to the unit 112; an electric current is then supplied to the energising winding 110 in such a direction that the movement is assisted, and stiffness of the bellows is compensated; again, the solenoid is initially calibrated in accordance with bellows stiffness or springiness by setting the system up with the bellows unsealed.

The non-linear compensating features in FIGS. 2, 3 and 4, and the movement-assisting means and capacitor position-sensor in FIGS. 5, 6 and 7 are all merely examples of typical systems. Other arrangements may also be used to apply the principle of the invention. Also, the movement-assisting means of FIGS. 5, 6 or 7 may be applied to the bellows in FIGS. 2, 3 or 4 to provide partial compensation and to allow the value of f in equation [6] to be set to a convenient value.

I claim:

1. A terrestrial refractometer comprising:
a gastight enclosure of substantially invariant transverse section and having a linearly movable endwall which varies in position in accordance with ambient temperature and pressure, the enclosure containing a fixed mass of a gas which at least approximates to an ideal gas; and
sensing and compensating means comprising a non-linear scale fixed to the movable endwall so as to respond to linear movement of the endwall, and an adjacent simple thermometer said thermometer being positioned with respect to said non-linear scale so that a level in said thermometer can act as a reference mark for reading said non-linear scale, whereby a compensating factor is derived which is proportional to the linear movement of the endwall from its position under conditions of standard temperature and pressure so that any resistance of the enclosure to movement of the endwall is compensated.

2. A terrestrial refractometer comprising:
a gastight enclosure of substantially invariant transverse section and having a linearly movable endwall which varies in position in accordance with ambient temperature and pressure, the enclosure containing a fixed mass of a gas which at leas approximates to an ideal gas; and sensing and compensating means comprising a plate fixed to the movable endwall so as to respond to linear movement of the endwall, the plate having in it a shaped slit; and light source; and a light detector, the shape of the slit being such that as the endwall moves, the amount of light received from the source by the detector varies non-linearly, whereby a compensating factor is applied which is proportional to the linear movement of the endwall from its position under conditions of standard temperature and pressure so that any resistance of the enclosure to movement of the endwall is compensated.

3. A terrestrial refractometer according to claim 2 further comprising a thermistor or thermocouple arranged to compensate for variations in ambient temperature.

4. A terrestrial refractometer comprising:
a gastight enclosure of substantially invariant transverse section and having a linearly movable endwall which varies in position in accordance with ambient temperature and pressure, the enclosure containing a fixed mass of a gas which at least approximates to an ideal gas; and
sensing and compensating means comprising an electrical capacitor having a first plate attached to the movable endwall so as to respond to linear movement of the endwall, a fixed second plate and capacitor-sensing means, the capacitor being arranged so that linear movement of the endwall causes a non-linear change in capacitance related to the force on said endwall, whereby a compensating factor is applied which is proportional to the linear movement of the endwall from its position under conditions of standard temperature and pressure so that any resistance of the enclosure to movement of the endwall is compensated.

5. A terrestrial refractometer comprising:
a gastight enclosure of substantially invariant transverse section and having a linearly movable endwall which varies in position in accordance with ambient temperature and pressure, the enclosure containing a fixed mass of a gas which at least approximates to an ideal gas; and
sensing and compensating means comprising movement-assistance means arranged to apply to the movable endwall a force in the direction of movement which is proportional to the magnitude of the movement, whereby a compensating factor is applied which is proportional to the linear movement of the endwall from its position under conditions of standard temperature and pressure so that any resistance of the enclosure to movement of the endwall is compensated.

6. A terrestrial refractometer according to claim 5 in which the movement assistance means is a pair of jaws attached to the fixed and movable endwalls of the bellows so as to assist both expansion and contraction.

7. A terrestrial refractometer according to claim 6 in which the movement of the jaws is controlled manually, there being also provided means to determine when the pressures inside and outside the bellows are equal.

8. A terrestrial refractometer according to claim 6 in which the movement of the jaws is controlled by a spring.

9. A terrestrial refractometer according to claim 6 in which the movement of the jaws is controlled by an electrical sensing and energising solenoid.

10. A terrestrial refractometer according to claim 5 in which the sensing means comprises an electrical capacitor arranged to sense the position of the movable endwall.

* * * * *